United States Patent [19]

Chen et al.

[11] 4,260,839

[45] Apr. 7, 1981

[54] ETHANE CONVERSION PROCESS

[75] Inventors: Nai Y. Chen, Titusville; Werner O. Haag, Lawrenceville; Tracy J. Huang, Trenton, all of N.J.

[73] Assignee: Mobil Oil Corporation, New York, N.Y.

[21] Appl. No.: 57,924

[22] Filed: Jul. 16, 1979

[51] Int. Cl.$^3$ .......................... C07C 9/04; C07C 2/12; C07C 6/10; B01J 29/30
[52] U.S. Cl. .................. 585/257; 48/196 A; 208/DIG. 2; 208/111; 208/135; 208/141; 252/455 Z; 252/477 R; 585/317; 585/319; 585/407; 585/415; 585/417; 585/708
[58] Field of Search ............... 585/257, 317, 407, 415, 585/417, 708; 252/477 R

[56] References Cited

U.S. PATENT DOCUMENTS

| 3,136,713 | 6/1964 | Miale et al. | 208/113 |
|---|---|---|---|
| 3,254,023 | 5/1966 | Miale et al. | 208/120 |
| 3,267,023 | 8/1966 | Miale et al. | 208/111 |
| 3,700,585 | 10/1972 | Chen et al. | 208/111 |
| 3,702,886 | 11/1972 | Argauer et al. | 423/328 |
| 3,709,979 | 1/1973 | Chu | 423/328 |
| 3,832,449 | 8/1974 | Rosinski et al. | 208/120 X |
| 4,070,411 | 1/1978 | Butter et al. | 585/257 X |
| 4,100,218 | 7/1978 | Chen et al. | 585/257 X |

Primary Examiner—Herbert Levine
Assistant Examiner—G. E. Schmitkons
Attorney, Agent, or Firm—Charles A. Huggett; Michael G. Gilman; Howard M. Flournoy

[57] ABSTRACT

A process for effecting an endothermic and an exothermic reaction, under conversion conditions, in a single reaction zone wherein ethane is endothermically converted to $C_3+$ hydrocarbons, and wherein an unconverted portion of ethane is simultaneously exothermically hydrogenated to methane in the presence of a catalyst system comprising a crystalline aluminosilicate zeolite having a uniform structure characterized by pores, the major dimension of which is less than 6 Angstroms and ZSM-5 type aluminosilicate zeolite, containing a minor amount of Zn in combination with a Group VIII noble metal or a Group IB metal, the exothermic reaction providing sufficient heat to maintain the reaction zone at a temperature capable of sustaining the endothermic reaction.

15 Claims, No Drawings

ETHANE CONVERSION PROCESS

BACKGROUND OF THE INVENTION

1. Field of the Invention

This application is directed to a process for producing LPG, gasoline and/or aromatics from ethane wherein ethane containing feeds are brought in contact with a novel catalytic system comprising a ZSM-5 type catalyst and a uniform narrow pore aluminosilicate crystalline catalyst, the largest dimension of said pores being less than about 6 Angstroms. In a single reaction zone a portion of the ethane in said feed is converted over the ZSM-5 type catalyst to $C_3+$ hydrocarbons, and a portion of the unconverted ethane is converted by reaction with by-product hydrogen to methane using the narrow pore crystalline catalyst, e.g., erionite.

2. Description of the Prior Art

U.S. Pat. Nos. 3,254,023 and 3,267,023 are directed to a catalytic method of carrying out an exothermic reaction and an endothermic reaction in a single reaction zone wherein the heat evolved in the exothermic reaction is utilized to effect the endothermic reaction. The catalyst used therein is a mixture of, e.g., a solid porous hydrogenation catalyst and a crystalline zeolite cracking catalyst. Further, U.S. Pat. No. 3,136,713 discloses a selective combustion process wherein a combustible mixture of molecules of differing molecular size are passed over a crystalline aluminosilicate catalyst.

SUMMARY OF THE INVENTION

This application is directed to an integrated process wherein a fluid feed or charge (fluid, as used herein, refers to either gaseous or liquid, or both) containing ethane is converted over a ZSM-5 catalyst to $C_3+$ hydrocarbons and simultaneously in the same reaction vessel a portion of unconverted ethane in said feed is converted to methane. In so far as is known the integration of the endothermic conversion process of ethane to $C_3+$ hydrocarbons, with a heat producing reaction wherein ethane is converted to methane is novel and the specific catalytic combination used therein is also thought to be novel.

Therefore, this application is more specifically directed to a process for effecting an endothermic reaction and an exothermic reaction in a single reaction zone comprising introducing into said reaction zone an ethane containing charge and causing ethane therein, while in said reaction zone, to simultaneously undergo said endothermic and said exothermic reaction by contacting said charge under reaction conditions with an admixture of a narrow pore crystalline aluminosilicate zeolite catalyst characterized by having a uniform structure characterized by pores, the major dimension of which is less than about 6 Angstroms with a ZSM-5 type crystalline aluminosilicate zeolite catalyst. The relative proportions of said catalysts are regulated so that the heat evolved from the exothermic reaction serves to maintain the reaction zone at a temperature sufficient to sustain the endothermic reaction. The application is also directed to the catalyst combination used in the above-described process.

DESCRIPTION OF SPECIFIC EMBODIMENTS

The process of this invention is therefore concerned with the conversion of ethane to $C_3+$ hydrocarbons, e.g., LPG, gasoline and/or aromatics in which said conversion which is endothermic is carried out simultaneously in a single reaction zone with an exothermic process wherein ethane is converted by by-product hydrogen to methane.

The above described process is usually carried out under the following operating conditions: temperature from about 1050° to about 1500° F., preferably from about 1200° to about 1400° F.; pressure from atmospheric to about 200 psig, preferably from about atmospheric to about 100 psig and a weight hourly space velocity (WHSV) of from about 0.2 to 2, preferably from about 0.2 to 1.

Catalysts especially suitable for the endothermic reaction are of the ZSM-5 type, preferably modified to contain Zn in combination with a noble metal from Group VIII and/or a Group IB metal. ZnPd-ZSM-5 and ZnCu-ZSM-5 are exemplary. Metal loading of 0.1 to 5 wt. % of each metal (preferably 0.3-2 wt. %) may be used. Catalysts suitable for the exothermic reaction are of the non-ZSM-5 type, preferably a narrow pore zeolite such as erionite, clinoptilolite, or ferrierite modified to contain a Group IIB metal, more specifically Zn-erionite, with 0.5 to 6 wt. % Zn (preferably 2-4 wt. %). The narrow pore zeolite is further characterized by pore windows of a size such as would be provided by 8-membered rings of oxygen atoms. The metal may be incorporated into the catalysts by any convenient process such as by impregnation, deposition or ion-exchange.

The relative proportions of the two catalyst materials may vary between 10:1 to 1:10, depending on their relative activity, with respect to obtaining a desired product. They may be in separate particles or each may be dispersed separately in a matrix material or they may also be combined with a matrix material to form a single particle.

The ZSM-5 type zeolite catalysts herein described are members of a novel class of zeolites exhibiting some unusual properties. These catalysts induce profound transformations of aliphatic hydrocarbons to aromatic hydrocarbons in commercially desirable yields and are generally highly effective in conversion reactions involving aromatic hydrocarbons. Although they have unusually low alumina contents, i.e., high silica to alumina ratios, they are very active even when the silica to alumina ratio exceeds 30. This activity is surprising since catalytic activity is generally attributed to framework aluminum atoms and cations associated with these aluminum atoms. These catalysts retain their crystallinity for long periods in spite of the presence of steam at high temperature which induces irreversible collapse of the framework of other zeolites, e.g., of the X and A type. Furthermore, carbonaceous deposits, when formed, may be removed by burning at higher than usual temperatures to restore activity. In many environments the zeolites of this class exhibit very low coke forming capability, conducive to very long times on stream between burning regenerations.

An important characteristic of the crystal structure of this class of zeolites is that it provides constrained access to, and egress from the intracrystalline free space by virtue of having a pore dimension greater than about 5 Angstroms and pore windows of about a size such as would be provided by 10-membered rings of oxygen atoms. It is to be understood, of course, that these rings are those formed by the regular disposition of the tetrahedra making up the anionic framework of the crystalline aluminosilicate, the oxygen atoms being bonded to the silicon or aluminum atoms at the centers of the tetrahedra. Briefly, the preferred type catalysts useful in this invention possess, in combination: a silica to alumina ratio of at least about 12; and a structure providing constrained access to the crystalline free space.

The silica to alumina ratio referred to may be determined by conventional analysis. This ratio is meant to represent, as closely as possible, the ratio in the rigid anionic framework of the zeolite crystal and to exclude aluminum in the binder or in cationic or other form within the channels. Although catalysts with a silica to alumina ratio of at least 12 are useful, it is preferred to use catalysts having higher ratios of at least about 30. Such catalyst, after activation, acquire an interacrystalline sorption capacity for normal hexane which is greater than that for water, i.e., they exhibit "hydrophobic" properties. It is believed that this hydrophobic character is advantageous in the present invention.

The type zeolites useful in this invention freely sorb normal hexane and have a pore dimension greater than about 5 Angstroms. In addition, the structure must provide constrained access to larger molecules. It is sometimes possible to judge from a known crystal structure whether such constrained access exists. For example, if the only pore windows in a crystal are formed by 8-membered rings of oxygen atoms, then access by molecules of larger cross-section than normal hexane is excluded and the zeolite is not of the desired type. Windows of 10-membered rings are preferred, although, in some instances, excessive puckering or pore blockage may render these catalysts ineffective. Twelve-membered rings do not generally appear to offer sufficient constraint to produce the advantageous conversions, although puckered structures exist such as TMA offretite which is a known effective zeolite. Also, structures can be conceived, due to pore blockage or other cause, that may be operative.

Rather than attempt to judge from crystal structure whether or not a catalyst possesses the necessary constrained access, a simple determination of the "constraint index" may be made by passing continuously a mixture of an equal weight of normal hexane and 3-methylpentane over a small sample, approximately 1 gram or less, of catalyst at atmospheric pressure according to the following procedure. A sample of the catalyst, in the form of pellets or extrudate, is crushed to a particle size about that of coarse sand and mounted in a glass tube. Prior to testing, the catalyst is treated with a stream of air at 1000° F. for at least 15 minutes. The catalyst is then flushed with helium and the temperature adjusted between 550° F. and 950° F. to give an overall conversion between 10% and 60%. The mixture of hydrocarbons is passed at 1 liquid hourly spaced velocity (i.e., 1 volume of liquid hydrocarbon per volume of catalyst per hour) over the catalyst with a helium dilution to give a helium to total hydrocarbon mole ratio of 4:1. After 20 minutes on stream, a sample of the effluent is taken and analyzed, most conveniently by gas chromatography, to determine the fraction remaining unchanged for each of the two hydrocarbons.

The "constraint index" is calculated as follows:

$$\text{Constraint Index} = \frac{\log_{10} (\text{fraction of n-hexane remaining})}{\log_{10} (\text{fraction of 3-methylpentane remaining})}$$

The constraint index approximates the ratio of the cracking rate constants for the two hydrocarbons. Catalysts suitable for the present invention are those having a constraint index in the approximate range of 1 to 12. Constraint Index (CI) values for some typical catalysts are:

| CAS | C.I. |
|---|---|
| ZSM-4 | 0.5 |
| ZSM-5 | 8.3 |
| ZSM-11 | 8.7 |
| ZSM-12 | 2 |
| ZSM-35 | 4.5 |
| ZSM-38 | 2 |
| TMA Offretite | 3.7 |
| Beta | 0.6 |
| H-Zeolon | 0.5 |
| REY | 0.4 |
| Amorphous Silica-Alumina | 0.6 |
| Erionite | 38 |

It is to be realized that the above constraint index values typically characterize the specified zeolites but that such are the cumulative result of several variables used in determination and calculation thereof. Thus, for a give zeolite depending on the temperature employed within the aforenoted range of 550° F. to 950° F., with accompanying conversion between 10% and 60%, the constraint index may vary within the indicated approximate range of 1 to 12. Likewise, other variables such as the crystal size of the zeolite, the presence of possibly occluded contaminants and binders intimately combined with the zeolite may affect the constraint index. It will accordingly be understood by those skilled in the art that the constraint index, as utilized herein, while affording a highly useful means for characterizing the zeolites of interest is approximate, taking into consideration the manner of its determination, with the probability, in some instances, of compounding variable extremes. However, in all instances, at a temperature within the above-specified range of 550° F. to 950° F., the constraint index will have a value for any given zeolite of interest herein within the approximate range of 1 to 12.

The class of zeolites defined herein is exemplified by ZSM-5, ZSM-11, ZSM-12, ZSM-35, ZSM-38 and other similar materials. Recently issued U.S. Pat. No. 3,702,886 describing and claiming ZSM-5 is incorporated herein by reference.

ZSM-11 is more particularly described in U.S. Pat. No. 3,709,979, the entire contents of which are incorporated herein by reference.

ZSM-12 is more particularly described in U.S. Pat. No. 3,832,449, the entire contents of which are incorporated herein by reference.

ZSM-38 is more particularly described in U.S. Application Ser. No. 528,060, filed Nov. 29, 1974. This zeolite can be identified, in terms of mole ratios of oxides and in the anhydrous state, as follows:

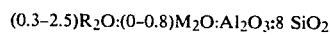

$$(0.3-2.5)R_2O:(0-0.8)M_2O:Al_2O_3:8\ SiO_2$$

wherein R is an organic nitrogen-containing cation derived from a 2-(hydroxyalkyl)trialkylammonium compound and M is an alkali metal cation and is characterized by a specified X-ray powder diffraction pattern.

In a preferred synthesized form, the zeolite has a formula, in terms of mole ratios of oxides and in the anhydrous state, as follows:

$$(0.4-2.5)R_2O:(0-0.6)M_2O:Al_2O_3:xSiO_2$$

wherein R is an organic nitrogen-containing cation derived from a 2-(hydroxyalkyl)trialkylammonium compound, wherein alkyl is methyl, ethyl or a combination thereof, M is an alkali metal, especially sodium and x is from greater than 8 to about 50.

The synthetic ZSM-38 zeolite possesses a definite distinguishing crystalline structure whose X-ray diffraction pattern shows substantially the significant lines set forth in Table I. It is observed that this X-ray diffraction pattern (significant lines) is similar to that of natural ferrierite with a notable exception being that natural ferrierite patterns exhibit a significant line at 11.33Å.

TABLE I

| d(Å) | I/I$_o$ |
|---|---|
| 9.8 ± 0.20 | Strong |
| 9.1 ± 0.19 | Medium |
| 8.0 ± 0.16 | Weak |
| 7.1 ± 0.14 | Medium |
| 6.7 ± 0.14 | Medium |
| 6.0 ± 0.12 | Weak |
| 4.37 ± 0.09 | Weak |
| 4.23 ± 0.09 | Weak |
| 4.01 ± 0.08 | Very Strong |
| 3.81 ± 0.08 | Very Strong |
| 3.69 ± 0.07 | Medium |
| 3.57 ± 0.07 | Very Strong |
| 3.51 ± 0.07 | Very Strong |
| 3.34 ± 0.07 | Medium |
| 3.17 ± 0.06 | Strong |
| 3.08 ± 0.06 | Medium |
| 3.00 ± 0.06 | Weak |
| 2.92 ± 0.06 | Medium |
| 2.73 ± 0.06 | Weak |
| 2.66 ± 0.05 | Weak |
| 2.60 ± 0.05 | Weak |
| 2.49 ± 0.05 | Weak |

A further characteristic of ZSM-38 is its sorptive capacity providing said zeolite to have increased capacity for 2-methylpentane (with respect to n-hexane sorption by the ratio n-hexane/2-methylpentane) when compared with a hydrogen form of natural ferrierite resulting from calcination of ammonium exchanged form. The characteristic sorption ratio n-hexane/2-methylpentane for ZSM-38 (after calcination at 600° C.) is less than 10, whereas that ratio for the natural ferrierite is substantially greater than 10, for example, as high as 34 or higher.

Zeolite ZSM-38 can be suitably prepared by preparing a solution containing sources of an alkali metal oxide, preferably sodium oxide, an organic nitrogen-containing oxide, an oxide of aluminum, an oxide of silicon and water having a composition, in terms of mole ratios of oxides, falling within the following ranges:

| R+ | Broad | Preferred |
|---|---|---|
| R+ + M+ | 0.2-1.0 | 0.3-0.9 |
| OH$^-$/SiO$_2$ | 0.05-0.5 | 0.07-0.49 |
| H$_2$O/OH$^-$ | 41-500 | 100-250 |
| SiO$_2$/Al$_2$O$_3$ | 8.8-200 | 12-60 | wherein R is an organic nitrogen-containing cation derived from a 2-(hydroxyalkyl)trialkylammonium compound and M is an alkali metal ion and maintaining the mixture until crystals of the zeolite are formed. (The quantity of OH is calculated only from the inorganic sources of alkali without any organic base contribution). Thereafter, the crystals are separated from the liquid and recovered. Typical reaction conditions consist of heating the foregoing reaction mixture to a temperature of from about 90° C. to about 400° C. for a period of time from about 6 hours to about 100 days. A more preferred temperature range is from about 150° C. to about 400° C. with the amount of time at a temperature in such range being from about 6 hours to about 80 days.

The digestion of the gel particles is carried out until crystals form. The solid product is separated from the reaction medium, as by cooling the whole to room temperature, filtering and water washing. The crystalline product is thereafter dried, e.g. at 230° F. for from about 8 to 24 hours.

ZSM-35 is more particularly described in U.S. application Ser. No. 528,061, filed Nov. 29, 1974. This zeolite can be identified, in terms of mole ratios of oxides and in the anhydrous state, as follows:

$$(0.3-2.5)R_2O:(0-0.8)M_2O:Al_2O_3:8\ SiO_2$$

wherein R is an organic nitrogen-containing cation derived from ethylenediamine or pyrrolidine and M is an alkali metal cation and is characterized by a specified X-ray powder diffraction pattern.

In a preferred synthesized form, the zeolite has a formula, in terms of mole ratios of oxides and in the anhydrous state, as follows:

$$(0.4-2.5)R_2O:(0-0.6)M_2O:Al_2O_3;xSiO_2$$

wherein R is an organic nitrogen-containing cation derived from ethylenediamine or pyrrolidine, M is an alkali metal, especially sodium and x is from greater than 8 to about 50.

The synthetic ZSM-35 zeolite possesses a definite distinguishing crystalline structure whose X-ray diffraction pattern shows substantially the significant lines set forth in Table II. It is observed that this X-ray diffraction pattern (with respect to significant lines) is similar to that of natural ferrierite with a notable exception being that natural ferrierite patterns exhibit a significant line at 11.33 Å. Close examination of some individual samples of ZSM-35 may show a very weak line at 11.3–11.5 Å. This very weak line, however, is determined not to be a significant line for ZSM-35.

TABLE II

| d(Å) | I/Io |
|---|---|
| 9.6 ± 0.20 | Very Strong-Very,Very Strong |
| 7.10 ± 0.15 | Medium |
| 6.98 ± 0.14 | Medium |
| 6.64 ± 0.14 | Medium |
| 5.78 ± 0.12 | Weak |
| 5.68 ± 0.12 | Weak |
| 4.97 ± 0.10 | Weak |
| 4.58 ± 0.09 | Weak |
| 3.99 ± 0.08 | Strong |
| 3.94 ± 0.08 | Medium Strong |
| 3.85 ± 0.08 | Medium |
| 3.78 ± 0.08 | Strong |
| 3.74 ± 0.08 | Weak |
| 3.66 ± 0.07 | Medium |
| 3.54 ± 0.07 | Very Strong |
| 3.48 ± 0.07 | Very Strong |
| 3.39 ± 0.07 | Weak |
| 3.32 ± 0.07 | Weak Medium |
| 3.14 ± 0.06 | Weak Medium |
| 2.90 ± 0.06 | Weak |
| 2.85 ± 0.06 | Weak |
| 2.71 ± 0.05 | Weak |
| 2.65 ± 0.05 | Weak |
| 2.62 ± 0.05 | Weak |

TABLE II-continued

| d(Å) | I/Io |
|---|---|
| 2.58 ± 0.05 | Weak |
| 2.54 ± 0.05 | Weak |
| 2.48 ± 0.05 | Weak |

A further characteristic of ZSM-35 is its sorptive capacity proving said zeolite to have increased capacity for 2-methylpentane (with respect to n-hexane sorption by the ratio n-hexane/2-methylpentane) when compared with a hydrogen form of natural ferrierite resulting from calcination of an ammonium exchanged form. The characteristic sorption ratio n-hexane/2-methylpentane for ZSM-35 (after calcination at 600° C.) is less than 10, whereas that ratio for the natural ferrierite is substantially greater than 10, for example, as high as 34 or higher.

Zeolite ZSM-35 can be suitably prepared by preparing a solution containing sources of an alkali metal oxide, preferably sodium oxide, an organic nitrogen-containing oxide, an oxide of aluminum, an oxide of silicon and water and having a composition in terms of mole ratios of oxides, falling within the following ranges:

| R+ | Broad | Preferred |
|---|---|---|
| R+ + M+ | 0.2–1.0 | 0.3–0.9 |
| OH$^-$/SiO$_2$ | 0.05–0.5 | 0.07–0.49 |
| H$_2$O/OH$^-$ | 41–500 | 100–250 |
| SiO$_2$/Al$_2$O$_3$ | 8.8–200 | 12–60 | wherein R is an organic nitrogen-containing cation derived from pyrrolidine or ethylenediamine and M is an alkali metal ion, and maintaining the mixture until crystals of the zeolite are formed. (The quantity of OH$^-$ is calculated only from the inorganic sources of alkali without any organic base contribution). Thereafter, the crystals are separated from the liquid and recovered. Typical reaction conditions consist of heating the foregoing reaction mixture to a temperature of from about 90° C. to about 400° C. for a period of time of from about 6 hours to about 100 days. A more preferred temperature range is from about 150° C. to about 400° C. with the amount of time at a temperature in such range being from about 6 hours to about 80 days.

The digestion of the gel particles is carried out until crystals form. The solid product is separated from the reaction medium, as by cooling the whole to room temperature, filtering and water washing. The crystalline product is dried, e.g., at 230° F., for from about 8 to 24 hours.

The specific zeolites described, when prepared in the presence of organic cations, are catalytically inactive, possibly because the intracrystalline free space is occupied by organic cations from the forming solution. They may be activated by heating in an inert atmosphere at 1000° F. for one hour, for example, followed by base exchange with ammonium salts followed by calcination at 1000° F. in air. The presence of organic cations in the forming solution may not be absolutely essential to the formation of this type zeolite; however, the presence of these cations does appear to favor the formation of this special type of zeolite. More generally, it is desirable to activate this type catalyst by base exchange with ammonium salts followed by calcination in air at about 1000° F. for from about 15 minutes to about 24 hours.

Natural zeolites may sometimes be converted to this type zeolite catalyst by various activation procedures and other treatments such as base exchange, steaming, alumina extraction and calcination, or combinations. Natural minerals which may be so treated include erionite, ferrierite, brewsterite, stilbite, epistilbite, heulandite and clinoptilolite.

The preferred crystalline aluminosilicates for the endothermic reaction are ZSM-5, ZSM-11, ZSM-12, ZSM-38 and ZSM-35, with ZSM-5 particularly preferred. However, as stated herein, it is contemplated to modify the ZSM-5 type zeolites for use herein with a minor amount of metal, i.e., a combination of Zn and a Group VIII noble metal or a Group IB metal. For the exothermic reaction erionite, clinoptilolite and ferrierite are preferred embodiments. Other such suitable narrow pore zeolites are selected from the group consisting of brewsterite, stilbite, epistilbite, heulandite, and chabazite. These non-ZSM-5 zeolites may be natural or synthetic and also may include a minor amount of metal selected from Groups IB, IIB and VIII of the Periodic Table.

The catalysts of this invention may be in the hydrogen form or they may be base exchanged or impregnated to contain ammonium or a metal cation complement. It is desirable to calcine the catalyst after base exchange. The metal cations that may be present include any of the cations of the metals of Groups I through VIII of the Periodic Table. However, in the case of Group IA metals, the cation content should in no case be so large as to effectively inactivate the catalyst.

In a preferred aspect of this invention, the catalysts for the endothermic reaction hereof are selected as those having a crystal framework density, in the dry hydrogen form, of not substantially below about 1.6 grams per cubic centimeter. It has been found that zeolites which satisfy these criteria are most desired because they tend to maximize the production of gasoline boiling range hydrocarbon products. Therefore, the preferred catalysts for the endothermic reaction in accordance with this invention are those having a constraint index as defined above of about 1 to about 12, a silica to alumina ratio of at least about 12 and a dried crystal density of not less than about 1.6 grams per cubic centimeter. The dry density for known structures may be calculated from the number of silicon plus aluminum atoms per 1000 cubic Angstroms, as given, e.g., on page 19 of the article of Zeolite Structure by W. M. Meir. This paper, the entire contents of which are incorporated herein by reference, is included in "Proceedings of the Conference on Molecular Sieves, London, April 1967", published by the Society of Chemical Industry, London, 1968. When the crystal structure is unknown, the crystal framework density may be determined by immersing the dry hydrogen form of the zeolite in an organic solvent which is not sorbed by the crystal. It is possible that the unusual sustained activity and stability of this class of zeolites is associated with its high crystal anionic framework density of not less than about 1.6 grams per cubic centimeter. This high density, of course, must be associated with a relatively small amount of free space within the crystal, which might be expected to result in more stable structures. This free space, however, is important as the locus of catalytic activity.

Crystal framework densities of some typical zeolites are:

| Zeolite | Void Volume | Framework Density |
| --- | --- | --- |
| Ferrierite | 0.28 cc/cc | 1.76 g/cc |
| Mordenite | .28 | 1.7 |
| ZSM-5,-11 | .29 | 1.79 |
| Dachiardite | .32 | 1.72 |
| L | .32 | 1.61 |
| Clinoptilolite | .34 | 1.71 |
| Laumontite | .34 | 1.77 |
| ZSM-4 (Omega) | .38 | 1.65 |
| Heulandite | .39 | 1.69 |
| P | .41 | 1.57 |
| Offretite | .40 | 1.55 |
| Levynite | .40 | 1.54 |
| Eriononite | .35 | 1.51 |
| Gmelinite | .44 | 1.46 |
| Chabazite | .47 | 1.45 |
| A | .5 | 1.3 |
| Y | .48 | 1.27 |

When synthesized in the alkali metal form, the zeolite is conveniently converted to the hydrogen form, generally by intermediate formation of the ammonium form as a result of ammonium ion exchange and calcination of the ammonium form to yield the hydrogen form. In addition to the hydrogen form, other forms of the zeolite wherein the original alkali metal has been reduced to less than about 1.5 percent by weight may be used. Thus, the original alkali metal of the zeolite may be replaced by ion exchange with other suitable ions of Groups IB to VIII of the Periodic Table including, by way of example, nickel, zinc, calcium or rare earth metals.

As noted hereinabove, the modifying treatment of metal loading of the zeolites is by any convenient method known to the art and forms no part of this invention.

The catalysts contemplated for use in the invention as embodied here can either be packed or fluid, fixed or moving. The endothermic heat of reaction converting ethane to $C_3+$ hydrocarbons is estimated to be between 15 and 30 kcal/mol of ethane. The methanation reaction generates about 17 kcal/mol of ethane. An approximately isothermal reaction is sustained by adjusting the catalyst composition and reaction against the endothermic reaction. Considerable variation in product distribution, while maintaining the reaction in heat balance, can also be achieved by adjusting catalyst compositions and conditions.

However typical product distribution from the ethane feed is as follows:

TABLE

| | (Ethane-Free Basis) | | | |
| --- | --- | --- | --- | --- |
| Wt. % | *Increasing Reaction Severity → | | | |
| Hydrogen | 0.6 | 0.5 | 0.7 | 0.8 |
| Methane | 42.7 | 53.3 | 58.2 | 65.9 |
| Propane+ Propylene | 40.9 | 23.5 | 14.0 | 0 |
| Aromatics | 15.8 | 22.7 | 27.1 | 33.4 |

*Mild reaction conditions include 1050° F., 1 atmospheric pressure and 2 WHSV. Increasing severity denotes higher temperatures, greater pressure and lower WHSV.

It is noted that more than 50% of ethane may be converted to $C_3+$ hydrocarbons when the demand for propane is high; more than 30% of ethane may be converted to an aromatics concentrate when little or no propane is produced.

In addition to the novelty of the integrated process, and the novelty of the catalytic combination or mixture described herein above and claimed below the direct conversion of ethane in the instant isothermal reaction system simplifies ethane conversion to a process comparable to a conventional naphtha pretreater or a distillate desulfurization process. Considerable savings in investment can be expected and the process can provide a significant new source of liquid hydrocarbons and petrochemicals in those locations where ethane is available at low cost.

It will be understood that the above description is merely illustrative of preferred embodiments of the invention, of which many variations may be made within the scope of the following claims by those skilled in the art without departing from the spirit thereof.

What we claim:

1. A process for simultaneously effecting an endothermic and an exothermic reaction in a single reaction zone comprising introducing into said reaction zone an ethane-containing charge, contacting said charge under reaction conditions with a mixture of a narrow pore crystalline aluminosilicate zeolite catalyst having a uniform structure characterized by pores, the major dimension of which is less than 6 Angstroms selected from the group consisting of erionite, ferrierite, brewsterite, stilbite, epistilbite, heulandite and clinoptilolite and chabazite and a ZSM-5 type crystalline aluminosilicate zeolite catalyst having a silica to alumina ratio of at least 12 and a constraint index in the approximate range of 1 to 12 each catalyst therein may be modified by the addition of a minor amount of a metal selected from Group IIB in combination with a metal from Group IB or Group VIII of the Periodic Table, and regulating the relative proportions of said catalysts so that the heat evolved from the exothermic reaction serves to maintain the reaction zone at a temperature sufficient to sustain the endothermic reaction, whereby ethane contacting said ZSM-5 type catalyst is converted to $C_3+$ hydrocarbons and a portion of unconverted ethane which is in contact with said narrow pore crystalline catalyst is converted by by-product hydrogen to methane.

2. The process of claim 1 wherein said catalysts are present in the reaction zone as separate catalytic particles or dispersed separately in a matrix material or combined with a matrix as a separate particle.

3. The process of claim 1 wherein said narrow pore catalyst is selected from the group consisting of erionite, ferrierite and clinoptilolite.

4. The process of claim 3 wherein said narrow pore catalyst is erionite.

5. The process of claim 1 wherein said catalyst contains from about 0.5 to about 6 wt. % of a Group IIB metal.

6. The process of claim 5 wherein said metal is zinc.

7. The process of claim 1 wherein the reaction conditions are as follows: temperature from 1050° to about 1500° F.; pressure from 1 atmospheric to about 200 psig and WHSV from 0.2 to about 2.

8. The process of claim 1 wherein said ZSM-5 type catalyst is selected from the group consisting of ZSM-5, ZSM-11, ZSM-12, ZSM-35 and ZSM-38.

9. The process of claim 8 wherein said ZSM-5 type catalyst is ZSM-5.

10. The process of claim 8 wherein said ZSM-5 type catalyst is ZSM-35.

11. The process of claim 8 wherein said ZSM-5 type catalyst is ZSM-38.

12. The process of claim 8 wherein the Group IIB metal is zinc, the Group VIII metal is a noble metal and the Group IB metal is copper.

13. The process of claim 8 wherein the ZSM-5 type catalyst contains from about 0.1 to 5 wt.% of Group IB metal in combination with a Group IIB or Group VIII metal or mixture thereof.

14. The process of claim 8 wherein the metal contained in said catalyst is selected from Zn-Pd and Zn-Cu.

15. The process of claim 1 wherein the relative proportion of said catalysts varies from about 10:1 to about 1:10.

* * * * *